United States Patent [19]
Witziers et al.

[11] Patent Number: 5,901,636
[45] Date of Patent: May 11, 1999

[54] COFFEE MAKER

[75] Inventors: Cornelis Witziers, Delft; Peter Dam, Hoogeveen; Marinus Bal, Zwinderen, all of Netherlands

[73] Assignee: U.S. Philips Corporation, New York, N.Y.

[21] Appl. No.: 08/988,702

[22] Filed: Dec. 11, 1997

[30] Foreign Application Priority Data

Dec. 23, 1996 [EP] European Pat. Off. .............. 96309399

[51] Int. Cl.$^6$ ........................................................ A47J 31/40
[52] U.S. Cl. ................................ 99/283; 99/285; 99/299; 99/307
[58] Field of Search ............................ 99/282, 283, 281, 99/285, 299, 304, 307

[56] References Cited

U.S. PATENT DOCUMENTS

| | | | |
|---|---|---|---|
| 3,179,035 | 4/1965 | Lockett | 99/282 |
| 3,527,172 | 9/1970 | Krueger et al. | 99/282 X |
| 5,388,501 | 2/1995 | Hazan et al. | 99/285 |

FOREIGN PATENT DOCUMENTS

2839140A1  3/1980  Germany .

Primary Examiner—Reginald L. Alexander
Attorney, Agent, or Firm—Ernestine C. Bartlett

[57] ABSTRACT

A coffee maker comprises a water reservoir, a water heating and supply device for supplying hot water to a filter device, the brewed coffee flowing from the filter device to a receptacle. The coffee maker includes a level detection circuit for detecting the water level in the reservoir, and this water level is used to control the brewing process so as to vary the flow of hot water to the filter device in dependence upon the water level in the reservoir. The water level may be used to control the power of a heating element in a continuous heater or may be used to control the operation of a pump in a pumped system.

6 Claims, 3 Drawing Sheets

COFFEE MAKER

BACKGROUND OF THE INVENTION

This invention relates to coffee makers.

There are various types of coffee maker used for brewing coffee. One type includes a water reservoir which supplies a water duct which is heated by a heating element. The heating process results in the formation of steam in the duct, and the resulting pressure conditions cause hot water to be forced up a riser tube into a coffee filter. Such a system has continuous heating of water in the duct during the brewing process, and this heating system will be referred to as a "continuous heater" in the following description.

Another type of coffee maker comprises a heated water reservoir, and hot water is supplied to a coffee filter under pressure by means of a pump. Espresso coffee machines also use pumped heating systems, and generally operate with higher system pressures.

This invention is equally applicable to all these types of coffee maker.

It is known that the coffee making cycle should be adaptable to the amount of coffee to be made. In particular, an optimum range of brewing times exists which provides a balance between the concentration of the coffee and the flavour. For this reason, the greater the quantity of coffee to be made, the higher should be the flow rate, so that the overall brewing time remains within the desired boundaries.

DE 2839140 discloses a coffee maker having a continuous heater, in which a manual selector is provided for indicating the quantity of coffee to be brewed, and the selection made determines the effective power of the heating element. In a continuous heater, such as that used in DE 2839140, the power supplied by the heating element determines the flow rate up the riser pipe.

SUMMARY OF THE INVENTION

According to the invention, there is provided a coffee maker for brewing coffee comprising a water reservoir, a water heating and supply device for supplying hot water to a filter device, the brewed coffee flowing from the filter device to a receptacle, wherein the coffee maker further comprises level detection means for detecting the water level in the reservoir, and wherein the water heating and supply device is controlled to vary the flow rate of hot water to the filter device in dependence upon the water level in the water reservoir.

The coffee maker of the invention provides automatic control of the brewing process so that the quality of brewed coffee is maintained irrespective of the amount of coffee to be brewed.

Preferably, the level detecting means monitors the water level, and the flow rate is controlled, during the brewing process. In this way, the flow rate of water to the filtering device may be controlled as the water level in the reservoir drops during brewing.

The invention is applicable to a coffee maker having a continuous heater, in which case the water heating and supply device comprises a heating element which heats water in a conduit coupling the water reservoir and the filter device, and the power of the heating element may then be controlled during the brewing process to vary the flow rate. The control of the power of the heating element is such that the flow rate is reduced as the water level in the reservoir drops. At the end of the brewing process, the flow rate of hot water to the filter device will always be set at the minimum level. This has the advantage that a temperature surge which takes place during thermal cut-out at the end of the brewing process is reduced. Furthermore, the noise which may be produced at the end of the brewing cycle because of this temperature surge is also reduced.

The heating element may comprise a plurality of heating members connected in parallel, at least one of which is disconnectable to enable adjustment of the heating element power.

The invention may also be applied to a pumped system, in which case the water heating and supply device comprises a heating element which heats the water in a heating chamber, and a pump which pumps water from the heating chamber to the filter device, wherein the electrical load on the pump is controlled during the brewing process to vary the flow rate.

The heating chamber may comprise the water reservoir, or may comprise an additional heating chamber.

The level detection means of the invention may comprise a float having a magnetic element, and at least one magnetic-field-responsive switch which is activated by the magnetic element when the water level is within predetermined levels.

Alternatively, various other level detection systems may be employed, such as capacitive level sensors, or a float which is associated with a potentiometer.

BRIEF DESCRIPTION OF THE DRAWINGS

The invention will now be described by way of example with reference to and as shown in the accompanying drawings in which.

DESCRIPTION OF PREFERRED EMBODIMENTS

Figure 1:
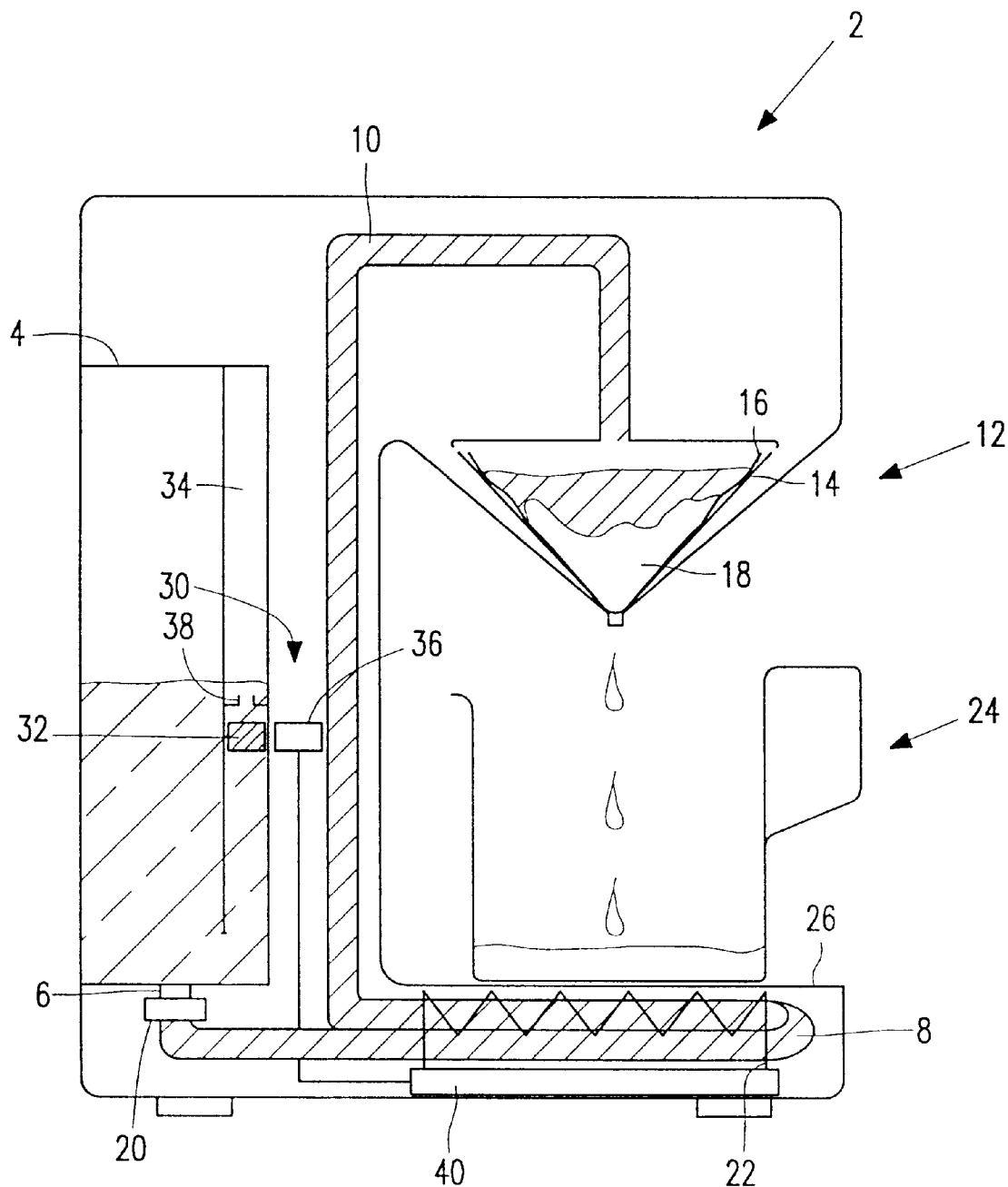
FIG. 1 shows a continuous heating type coffee maker according to the invention.

FIG. 1 shows a coffee maker having a continuous heater and which uses a level detection according to the invention. The coffee maker 2 comprises a water reservoir 4 having an outlet 6 which supplies a heating conduit 8 where water heating takes place. The heating conduit 8 is connected to a riser pipe 10 which discharges water above a filter device 12. The filter device 12 comprises a support 14 for a filter 16 for the coffee 18.

During use of the coffee maker 2 shown in FIG. 1, water flows from the reservoir 4 into the heating conduit 8 through a non-return valve 20. The water within the conduit 8 is heated by a heating element 22 which causes vaporisation of water within the conduit 8. This creates pressure within the conduit 8 driving heated water up the riser pipe 10 and into the filter device 12. Within the filter device 12, the water passes through the coffee 18 and into a receptacle 24. The coffee in the receptacle 24 is kept hot by the base 26 within which the heating element 22 is housed. The operation of the coffee maker as described so far is conventional. The heating element 22, conduit 8 and riser pipe 10 together constitute a water heating and supply device.

The invention provides a level detection circuit 30 for detecting the water level within the reservoir 4. In example shown in FIG. 1, the level detection circuit comprises a float 32 provided within a vertical channel 34. The float includes a magnetic portion which interacts with a magnetic reed switch 36 (or Hall sensor) at a particular level. A stop 38 limits the upward movement of the float 32 so that the float 32 interacts with the reed switch 36 for all water levels within the reservoir 4 above a predetermined level. Thus, the level detection circuit 30 provides a binary output representing a high or low water level.

The level detection circuit 30 is connected to, or comprises part of, the control circuit 40 of the heating element 22, so that the water level within the reservoir 4 determines the operation of the heating element 22.

For high water levels in the reservoir 4 the heating element 22 is operated with a higher power than when the water level in the reservoir 4 is at a low level. The power of the heating element 22 determines the pressure conditions within the heating conduit 8, and thereby determines the flow rate up the riser pipe 10. Consequently, the control of the heating element 22 may be used to alter the flow rate of water to the filter device 12 depending upon the water level. This has been found to be desirable so that the brewing time for the coffee may be maintained within predetermined boundaries which provide a desired balance between the strength and the flavour of the brewed coffee for optimal taste.

The level detection circuit 30 preferably monitors the water level in the reservoir 4 during the brewing process, namely as the water level drops. Thus, the flow rate may be controlled during the brewing process so that switching takes place as the water level in the reservoir drops. This has the advantage that the lower flow rate is always implemented at the end of the brewing process. The brewing process ends when all water in the reservoir 4 has been heated by the heating element 22, and a thermostatic switch detects a rise in the temperature in the vicinity of the heating element which is caused by the absence of water. This causes the heating element circuit to switch off, but there is a continued rise in temperature within the heating conduit 8 for some time after the circuit is switched off. This results in a high temperature surge at the end of the brewing process and produces undesirable noise. By ensuring that the heating element is switched to a low power at the end of the brewing process, the temperature surge and the noise are both reduced.

Figure 2:
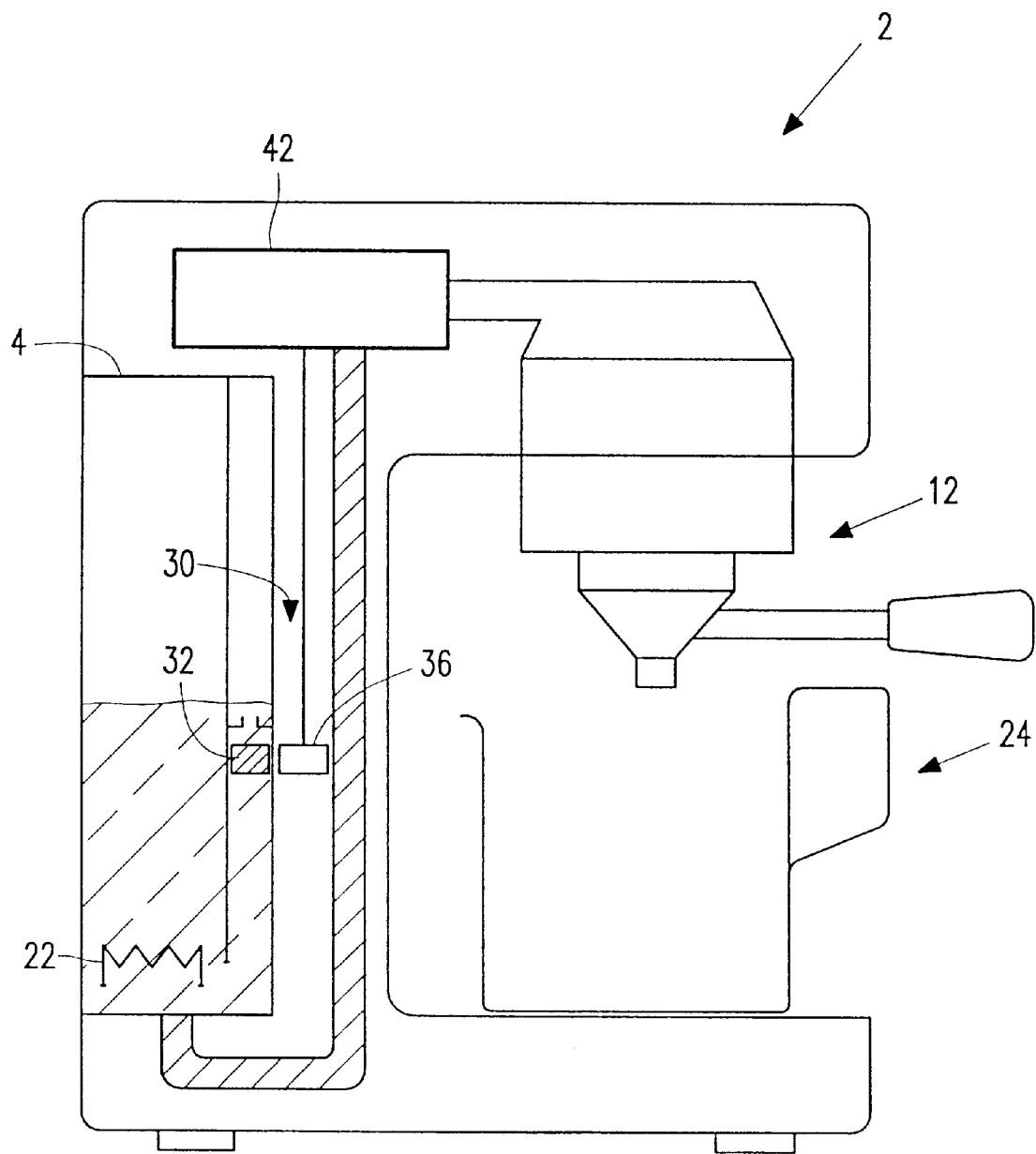
FIG. 2 shows a pumped coffee maker according to the invention.

FIG. 2 shows a pumped coffee maker 2 which also incorporates a level detection system of the invention. Similar components to the system shown in FIG. 1 have been given the same reference numerals. In the system of FIG. 2, water in the reservoir 4 is initially heated by the heating element 22 before being pumped to the filter device 12 by a pump 42. In this case, the heating element constitutes a water heating device, and the pump constitutes a water supply device. The pump 42 may only be operated once the temperature of the water in the reservoir 4 has reached the required temperature. The heating element is controlled thermostatically to maintain the desired water temperature. The heating element 22 may alternatively be provided in a separate heating chamber (which is smaller than the reservoir 4) but again the water is only pumped once it has reached the desired temperature. In the embodiment shown in FIG. 2 the level detection circuit 30 is connected to, or forms part of, the control circuit for the pump 42, so that the pump flow rate may be adjusted depending upon the water level within the reservoir 4. As will be described in the following, the flow rate may be controlled by varying the speed of the pump through control of the electrical load connected in the pump control circuit, or alternatively the flow rate may be controlled by introducing a variable flow constriction such as a valve. The level detection circuit shown in FIG. 2 is identical to that of FIG. 1 and again provides a binary signal for indicating a high or low water level within the reservoir 4.

Figure 3:
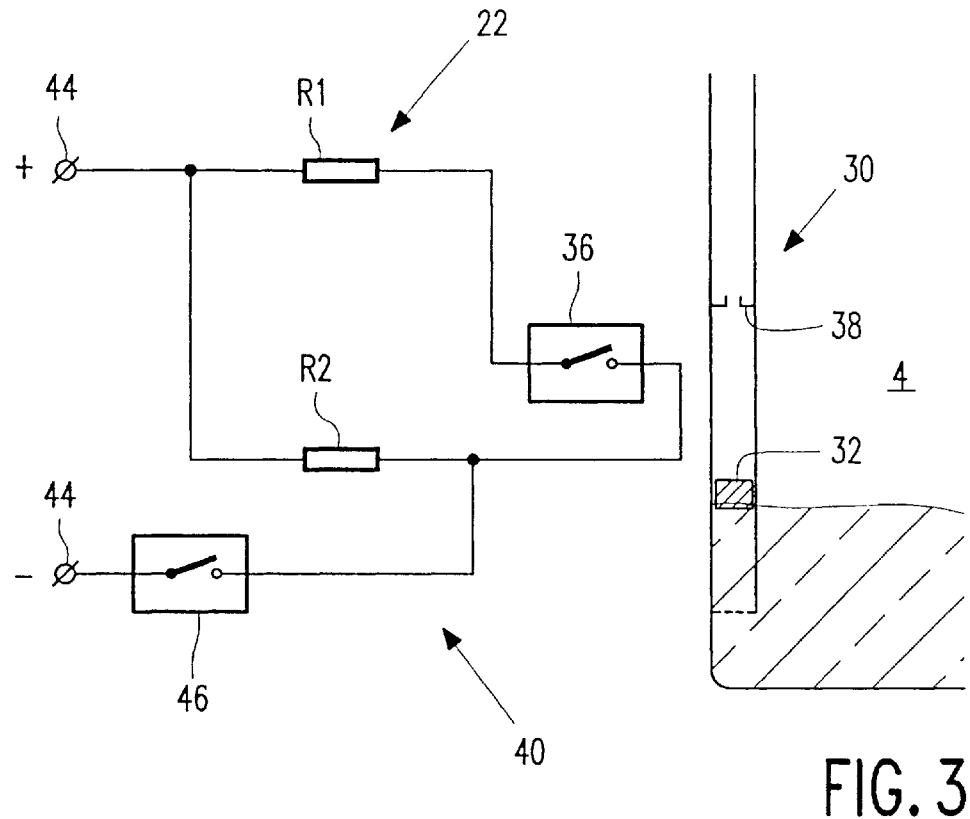
FIG. 3 shows a circuit for controlling the heating element of the coffee maker of FIG. 1.

FIG. 3 shows in greater detail how the level detection circuit 30 may be used to control the operation of the heating element 22 in the embodiment of FIG. 1. As shown, the heating element 22 comprises two heating members R1, R2 connected in parallel between power lines 44. One of the heating members R1 is connected in series with the magnetic reed switch 36 so that the heating member R1 may be switched in and out of the heating control circuit 40. The switch 36 is represented in FIG. 3 is a normally-open switch, so that when the float 32 is at the level of the stop 38 (i.e. for all high liquid levels), the magnetic coupling between the float 32 and the switch 36 causes the switch 36 to close. This maintains the heating member R1 in the circuit, and causes a high overall power of the heating element 22. For example, the heating member R1 may have a power of 0.9 KW, and the heating member R2, which is permanently connected, may have a power of 0.5 KW. The thermostatic control is represented schematically as switch 46.

The heating element 22 may alternatively comprise a single element, and the voltage applied to the terminals may be adjusted to regulate the power. As a further alternative, the effective power of a single heating element may be adjusted by varying the duty cycle governing the operation of the element.

The heating element 22 may comprise an immersion type heating element, or it may comprise a printed heating track for example on the base of the water reservoir.

Figure 4:
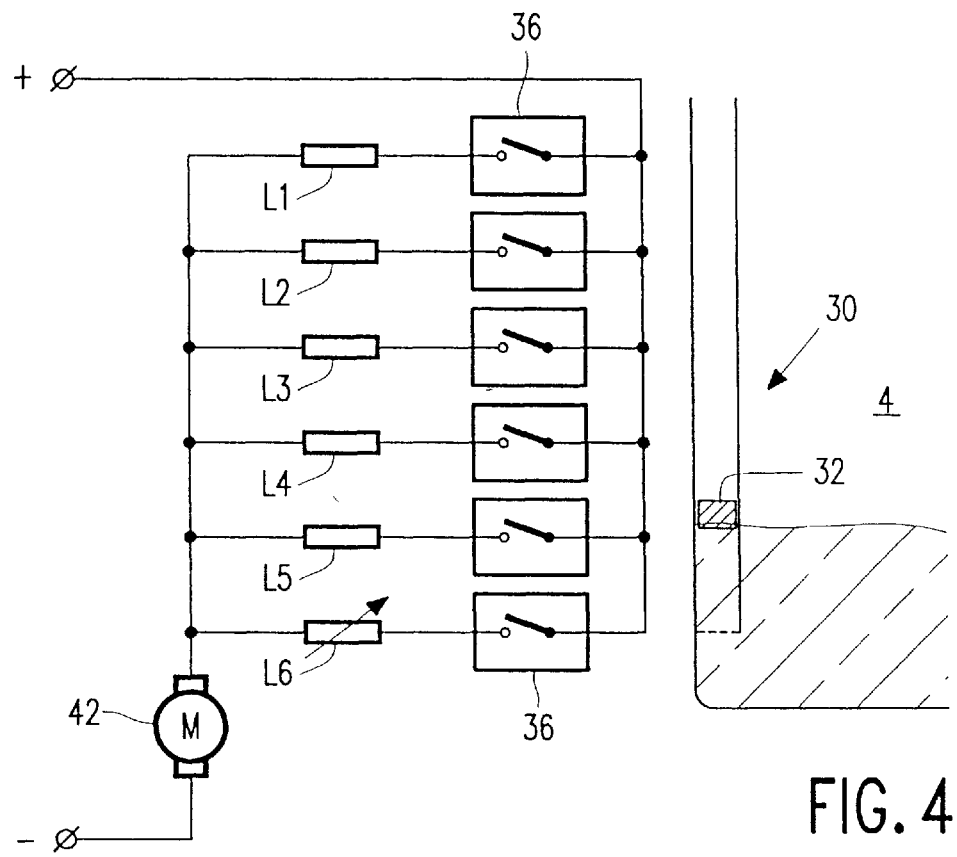
FIG. 4 shows a circuit for controlling the pump of the coffee maker of FIG. 2.

Although level control which provides only two signals has been described, it is of course equally possibly to provide a level detection enabling more accurate level measurement. FIG. 4 shows a circuit which enables more accurate level detection, and which is appropriate for a pumped coffee maker such as that shown in FIG. 2. In FIG. 4, the float 32 interacts with one of a number of normally open reed switches (or all Hall sensors) 36. The control circuit for the pump 42 comprises a load connected in series with the pump 42 which is variable depending upon the water level in the reservoir 4. In FIG. 4, the load comprises a permanently connected load resistor L6 which is coupled in parallel with one of the further load resistors L1 to L5 in dependence upon the water level. The position of the float 32 determines which switch 36 is closed by magnetic coupling, and thereby determines the overall load connected in series with the pump 42. This series-connected load determines the speed of the pump 42, and thereby determines the flow of water to the filter 12.

As an alternative to controlling the electrical load of the pump, the mechanical load for the pump may be controlled by introducing a variable flow constriction such as a valve, which is controlled by the level sensor signal.

Although a level sensor relying upon magnetic coupling between a floating magnet and a switch responsive to magnetic fields has been described, various other level detection circuits may be employed. For example, a float may mechanically activate a potentiometer circuit to adjust a resistor value in order to obtain the desired pump control, or heating element control. As a further alternative, capacitive level sensors are known in which the water in the reservoir 4 acts as a dielectric, to enable capacitive level measurement. Various other possibilities known in the field of fluid level measurement will be known to those skilled in the art.

We claim:

1. A coffee maker for brewing coffee comprising a water reservoir, a water heating and supply device for supplying hot water to a filter device, the brewed coffee flowing from the filter device to a receptacle, characterized in that the coffee maker further comprises level detection means for detecting the water level in the water reservoir during the brewing process and the supply device is controlled to vary the flow rate of hot water to the filter device in dependence upon the water level in the water reservoir during the brewing process.

2. A coffee maker as claimed in claim 1, wherein the water heating and supply device comprises a heating element which heats water in a conduit coupling the water reservoir and the filter device, and wherein the power of the heating element is controlled during the brewing process to vary the flow rate.

3. A coffee maker as claimed in claim 2, wherein the heating element comprises at least two heating members connected in parallel, at least one of which may be disconnected to enable adjustment of the heating element power.

4. A coffee maker as claimed in claim 1, wherein the water heating and supply device comprises a heating element which heats the water in a heating chamber, and a pump which pumps water from the heating chamber to the filter device, and wherein the electrical load on the pump is controlled during the brewing process to vary the flow rate.

5. A coffee maker as claimed in claim 4, wherein the heating chamber comprises the water reservoir.

6. A coffee maker as claimed in any preceding claim 1, wherein the level detection means comprises a float having a magnetic element and at least one magnetic-field-responsive switch, which is actuated by the magnetic element when the water level is between predetermined levels.

* * * * *